United States Patent [19]

Horikoshi et al.

[11] Patent Number: 5,246,839
[45] Date of Patent: Sep. 21, 1993

[54] SECRETION PLASMID COMPRISING THE KILGENE

[75] Inventors: Koki Horikoshi; Toshiaki Kudo, both of Tokyo, Japan; Tetsuo Kobayashi, Highland Park, N.J.; Chiaki Kato, Oomiya, Japan

[73] Assignee: Rikagaku Kenkyusho, Japan

[21] Appl. No.: 946,038

[22] Filed: Sep. 15, 1992

Related U.S. Application Data

[63] Continuation of Ser. No. 557,983, Jul. 26, 1990, abandoned, which is a continuation of Ser. No. 891,242, Jul. 29, 1986, abandoned.

[30] Foreign Application Priority Data

Jul. 30, 1985 [JP] Japan .................. 60-168288

[51] Int. Cl.$^5$ .................. C12P 21/02; C12P 19/34; C12N 15/00; C12N 1/21; C07K 3/00; C07H 15/12
[52] U.S. Cl. .................. 435/69.1; 435/172.3; 435/320.1; 435/252.3; 435/252.33; 435/200; 435/209; 530/300; 530/350; 935/29; 935/41; 935/56; 935/61; 935/73
[58] Field of Search .................. 435/69.1, 91, 172.3, 435/320.1, 252.3, 252.33; 530/300, 350; 536/27; 935/29, 41, 56, 61, 73

[56] References Cited

U.S. PATENT DOCUMENTS 4,624,922 11/1986 Horikoshi et al. ................ 435/172.3
4,948,735 8/1990 Luria et al. ........................ 435/252.8

OTHER PUBLICATIONS

Sashihera et al. J. Bacteriol. vol. 158 pp. 5903-506. (1984).
Kobayashi et al. J. Bacteriol. vol. 166, pp. 728-732 (1986).
Kudo et al. J. Bacteriol. vol. 156 pp. 949-951. (1983).
Chan et al. J. Biol. Chem. vol. 260 pp. 8925-8935 (1985).
Sabik et al. J. Bacteriol. vol. 153 pp. 1479-1485 (1983).
Neidhardt, Ed.-in-chief, *Escherichia Coli and Salmonello Typhimurium, Cellular and Molecular Biology*, vol. 2, pp. 1615-1624 only one re submitted pp. 1615-1619 were considered.

*Primary Examiner*—Joan Ellis
*Attorney, Agent, or Firm*—Dressler, Goldsmith, Shore, Sutker & Milnamow, Ltd.

[57] ABSTRACT

The present invention provides for a plasmid, pEAP7ΔP, containing a DNA region capable of inducing extracellular secretion of a useful, physiologically active substance in transformed host and a promoter DNA region regulating expression of the first DNA region. The present invention further provides for a microorganism transformed with the plasmid and a process for the production of the substances by culturing the microorganism.

13 Claims, 4 Drawing Sheets

FIG. 2

K GENE

```
ATGAGGAAAAGATTTTTGTGGAATATTCGCGATAAAC CTCCTTGTTGGATGT
MetArgLysArgPhePheValGlyIleIlePheAlaIleAsn LeuLeuVal GlyCys
```

I

```
                          90
CAGGCTAACTATATACGT GATGTTCAGGGAGGGGACCATCGCCACCATCCTCC
GlnAlaAsnTyrIleArg AspValGlnGlyGlyThrIleAlaProSerSer
```

II

```
                                    138
TCTTCTAAACTGACGGGGGATCGCGGTTCAGTAG
SerSerLysLeuThrGlyIleAlaVal Gln***
```

III

FIG. 3

```
Hinc II                         Ex PROMOTER              -35 EcoRV         60
GTCAACAATA TGAACTGTCA CAAATCTTAT ATATATATTG TGA[ATTGATAT]CACATCACTT
                                         -10                             120
TTTTTCAATG GG[TATTAT]GC TTAAGGTGTA ATGAATGATT GGGAGAGGGT GGGATGATAT
                        ──→ mRNA
                                 SD. SEQUENCE                            180
GTTTGTTTAT CAATGTGAAC AAAGCCAACA [GGCGG]TTGTA AGTAATGG[TG]TTTGTGGC
                                                                         240
GAAGAATGAA ACGATTGCCGA GTTACAAGA TACGATTGTG TTTGGGCTAA AAGGAATTGC
                                                                         300
AGCTTATCGC ACACATGCTG CTCAGCTAGG GTATACGGAT GCATTTGTAG ATGCTACAAC
HindIII 311                                           ┌─────────┐  ↑
ACAAGAAGCT T──────────────────────────────────────────│ K GENE  │──
                                                      └─────────┘
```

SECRETION PLASMID COMPRISING THE KILGENE

CROSS REFERENCE TO RELATED APPLICATION

This application is a continuation of application Ser. No. 07/557,983, filed Jul. 26, 1990, now abandoned, which, in turn, is a continuation of application Ser. No. 06/891,242, filed Jul. 29, 1986, now abandoned.

FIELD OF THE INVENTION

The present invention relates to a novel plasmid and a novel microorganism transformed therewith.

BACKGROUND OF THE INVENTION

Plasmids are extrachromosomal genes of cyclic DNA found in microorganism cells. Plasmids are currently being used as a means of genetic recombination of microorganisms and are becoming increasingly important in research in the fermentation industry.

Studies have recently been made in the plasmids containing foreign DNA coding for metabolic products or for particular growth requisites of microorganisms, such as amino acids or peptides. Some plasmids have been introduced into host microorganisms to obtain transformants.

The present inventors succeeded in constructing a novel plasmid into which DNA coding for the secretion (extracellular production) of penicillinase was inserted. This DNA was prepared from chromosomal DNA of a microorganism belonging to the genus Bacillus. The present inventors further succeeded in obtaining a novel and useful transformant, *Escherichia coli* HB101 (pEAP2), by introducing the above plasmid into the HB101 strain of *Escherichia coli* (Japanese Patent Publication (unexamined) 162886/1984).

Further, the present inventors succeeded in constructing a novel plasmid into which DNA coding for the secretion of xylanase was inserted, which DNA was prepared from chromosomal DNA of a microorganism belonging to the genus Bacillus. A novel and useful transformant, *Escherichia coli* HB101 (pCX 311) was then obtained by introducing the above plasmid into the HB101 strain of *Escherichia coli* (Japanese Patent Publication (unexamined) 126085/1985).

Then, the present inventors succeeded in constructing a novel plasmid by inserting a DNA fragment coding for production of a desired useful, physiologically active substance into a plasmid in which DNA coding for secretion of penicillinase had been inserted and, further, succeeded in obtaining a novel and useful transformant, Escherichia coli HB101 (pXP102-3), by introducing the above plasmid into the HB101 strain of *Escherichia coli*. (Japanese Patent Application 278681/1984).

Methods as mentioned above are very useful where a plasmid having an inserted DNA fragment coding for the secretion of a useful, physiologically active substance is introduced into a host organism to transform the host organism. The resultant transformant is cultured to allow for secretion and accumulation of the useful, physiologically active substance outside the cell, which substance is then isolated and collected. Advantages of such methods include maintenance of transformant viability, the absence of intracellular substance accumulation with feed-back inhibition of substance production and easy purification of the secreted substance.

At present, only a limited number of microorganisms are known to secrete desirable, useful, physiologically active substances outside a cell.

*Escherichia coli* (*E. coli*), which has been widely used as a host organism in gene recombination, and which has been studied in detail, is not known to primarily secrete its product outside the cells. The same properties are exhibited by transformants of *E. coli*.

On the other hand, *Bacillus subtilis*, which is one of the typical bacterial of the genus Bacillus, produces and secretes enzymes. However, it is genetically unstable, i.e., its genotype has a tendency to change. Further, its products are often decomposed by a protease produced by the microorganism itself.

Accordingly, microorganisms capable of producing and secreting desired, useful, physiologically active substances have great utility in industry. In particular, there is a need for a new transformant of *E. coli*, which is capable of secreting a product.

The present inventors have investigated the question of what gene plays a role in controlling extracellular secretion and have identified both a DNA region capable of inducing the extracellular secretion of useful, physiologically active substances in a transformed host and a promoter DNA region, which regulates expression of the former DNA region. Further, the inventors have succeeded in constructing a novel plasmid having these DNA regions and obtaining a novel microorganism transformed with the novel plasmid.

SUMMARY OF THE INVENTION

One aspect of the present invention provides for a plasmid having a DNA region, which is capable of inducing the extracellular secretion of a useful, physiologically active substance in transformed host, and a promoter DNA region, which regulates expression of the former DNA region.

The present invention further provides for a plasmid, which is constructed by inserting a DNA fragment coding for a particular, useful, physiologically active substance into the above plasmid.

In a further aspect, the invention provides for a microorganism, which is transformed with this plasmid.

The invention further provides for a process for the production of a useful, physiologically active substance by culturing the above transformant.

BRIEF DESCRIPTION OF THE ACCOMPANYING FIGURES

FIG. 2 shows the base sequence and amino acid sequence of a kil gene, which is designated "K gene".

FIG. 3 shows the base sequence of Ex promoter region for the K gene. The notation "S.D. SEQUENCE" indicates the Shine-Dalgano sequence.

Figure 4:
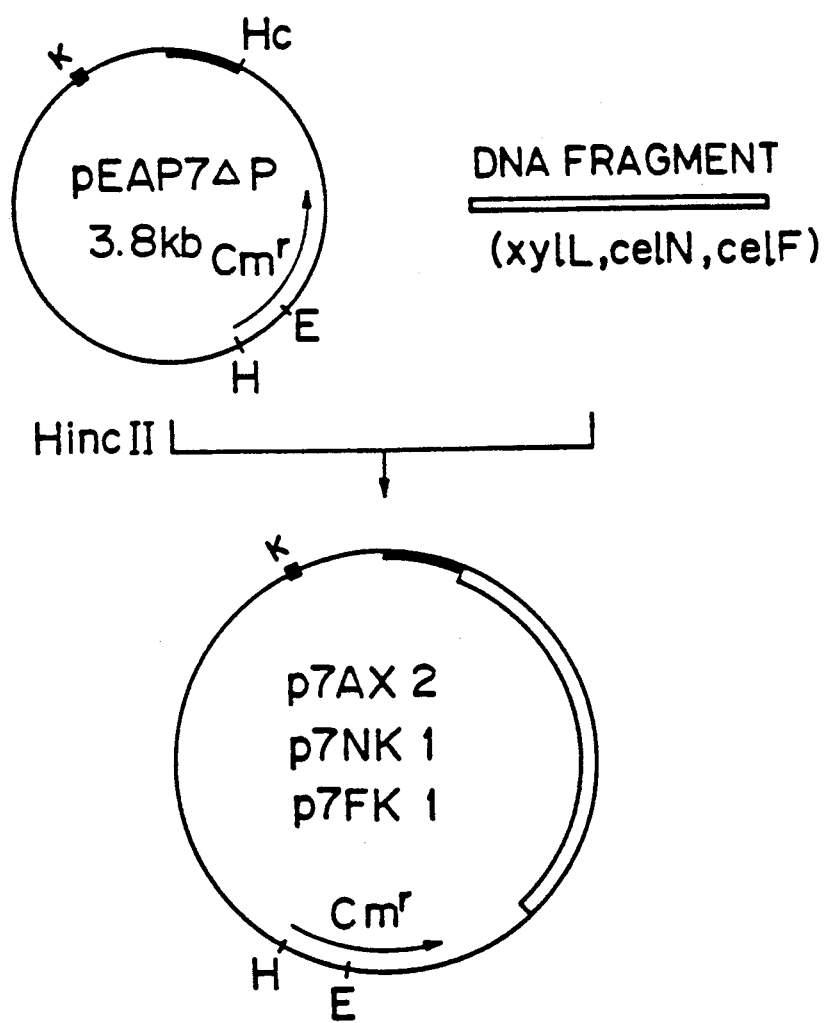

FIG. 4 schematically illustrates the insertion site of xylanase DNA (xylL) or cellulase DNA (cel N or cel F) into vector plasmid pEAP7ΔP.

DETAILED DESCRIPTION OF THE INVENTION

"Useful, physiologically active substance", as used herein, means a high-molecular weight, physiologically active substance, for instance, enzymes such as penicillinase, xylanase, β-galactosidase, β-lactamase, alkaline phosphatase and cellulase, peptide type hormones, such as insulin, human growth hormone, somatostatin, secretion and endorphins, and immunologically active substances, such as interferons and thymosin.

According to a preferred embodiment of the invention, a plasmid is provided which has a DNA region derived from plasmid pMB9, which region is capable of inducing the extracellular secretion of a useful, physiologically active substance in a transformed host, as well as a DNA region derived from chromosomal DNA of *Bacillus sq.* No. 170 that functions as a promoter DNA region to regulate expression of the former DNA region.

According to a more preferred embodiment, a plasmid is provided wherein the DNA region derived from plasmid pMB9 is a kil gene (hereinafter referred to as "K gene"), and the DNA region derived from the chromosomal DNA of *Bacillus sq.* No. 170 is a DNA region that is restricted by restriction enzymes, Hind III - Hinc II. One typical example of such a plasmid is a plasmid pEAP7ΔP.

Plasmid pMB9 is derived from pMB1 (see Bolivar et al., Gene 2:75-93 (1977)), which contains the K gene (Sabik et al., J. Bacteriology 153:1479–1485 (1983)), and which is responsible for colicin El release by cell lysis. However, the K gene cannot be expressed in pMB9 because the pMB9 plasmid lacks both the gene for colicin El production and its promoter gene, both of which are necessary for K gene expression. K gene is similar to Col El. Sabik et al. also reported that K gene of Col El is required for mitomycin-induced lethality and release of colicin.

Construction Of Plasmid pEAP7ΔP

Plasmid pEAP7ΔP may be obtained from, for instance, plasmid pEAP1, as mentioned below. Plasmid pEAP1 is a plasmid which was previously constructed by the present inventors and may be obtained as follows.

Construction Of Plasmid pEAP1

Chromosomal DNA of *Bacillus sq.* No. 170 (FERM BP-467), coding for penicillinase, is cleaved by a restriction enzyme, EcoRI, and the produced DNA fragments are inserted into an EcoRI site of a vector plasmid, pMB9, by a shotgun method. The resulting plasmid is then introduced into the HB101 strain of *E. coli* and screened for resistance to ampicillin (Ap) and sensitivity to tetracycline (Tc). Plasmid pEAP1 is isolated from the resultant transformants (Journal Of Bacteriology, Nov. 1983, p. 949-951).

Plasmid pEAP3

During passage of the HB101 *E. coli* harboring plasmid pEAP1, a mutant ($Ap^r.Tc_s$) is obtained. A plasmid is prepared from the mutant according to a conventional technique (F. Bolivar et al., Gene, 2, 95 (1977)), and plasmid pEAP3, which lacks about 4 kb upstream of structural gene of penicillinase (pen), is obtained.

Construction Of Plasmid pEAP6

Plasmid pEAP6 is cleaved by restriction enzymes, EcoRI and Hind III, treated by *E. coli* DNA polymerase I (Klenow fragment), (Molecular Cloning, A Laboratory Manual, p. 113 (1982)) to change the cleavage face to a flush end and ligated by DNA ligase T4. The resultant DNA is introduced into the HB101 strain of *E. coli* by, for instance, a $CaCl_2$ treatment method (E. M. Lederberg and S. N. Cohen, J. Bacteriol., 119, 1072 (1974)) to produce an Ap transformant by a technique similar to that mentioned above to obtain plasmid pEAP6, which plasmid lacks an EcoRI - Hind III DNA fragment of about 1 kb.

Construction Of Plasmid pEAP7

To obtain a chloramphenicol resistant ($Cm^r$) gene for use as a genetic marker, plasmid pBR329 (Louis Covarrubias and Francisco Bolivar, Gene, 17, 79–89 (1982)) is digested by restriction enzyme Acc II, and an Acc II DNA fragment of 1.3 kb is collected. Plasmid pEAP6 is digested by restriction enzyme Sma I, mixed with the above Acc II DNA fragment, subjected to a coupling reaction by DNA ligase T4, and then introduced into *E. coli* HB101 to transform it in a similar way as mentioned above. A chloramphenicol and ampicillin resistant transformant is separated, and a plasmid is prepared by a conventional technique, as mentioned above, to obtain plasmid pEAP7.

Construction Of Plasmid pEAP7ΔP

Plasmid pEAP7ΔP is digested by Hinc II to delete a Hinc II DNA fragment of 2.3 kb, subjected to a coupling reaction by DNA ligase T4, and then introduced into *E. coli* HB101 to transform it in a similar way, as mentioned above. Then, an ampicillin sensitive strain is separated from Chloramphenicol resistant ($Cm^r$) transformants, and a plasmid is prepared by a conventional technique, as mentioned above, to obtain plasmid pEAP7ΔP.

Figure 1:
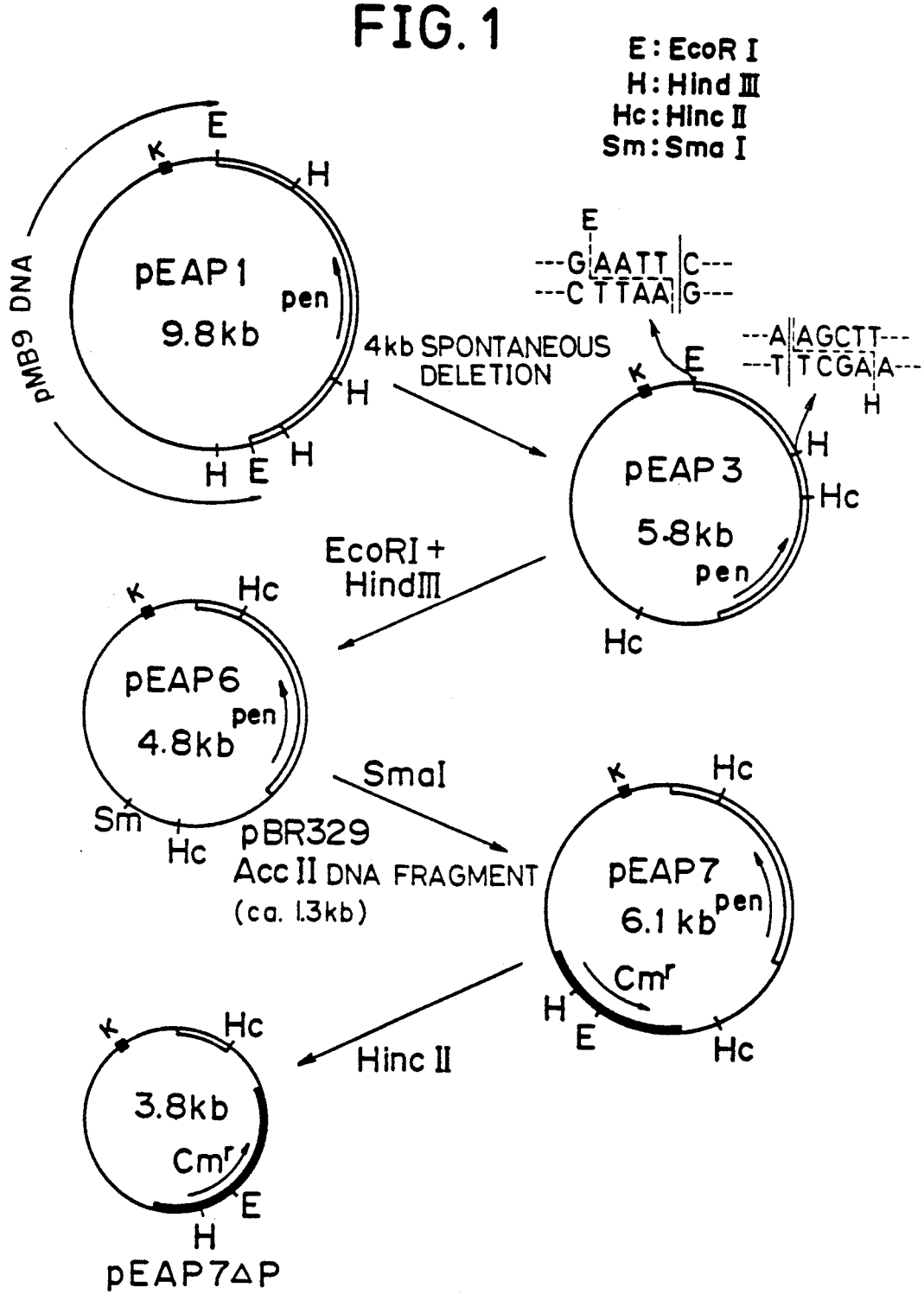
FIG. 1 shows the procedural steps for constructing plasmid pEAP7ΔP, together with a restriction endonuclease cleavage map.

The above procedural steps are schematically shown in FIG. 1.

Plasmid pEAP7ΔP thus obtained is a cyclic DNA molecule of 3.8 kb which contains a first DNA region (designated as K gene) capable of inducing extracellular secretion of useful, physiologically active substances in a transformed host; a second promoter DNA region which regulates expression of the K gene (Hind III - Hinc II DNA region, about 0.3 kb, designated Ex promoter); and a $Cm^r$ DNA as a genetic marker. This plasmid has only one Hinc II site. FIG. 2 shows the base sequence and amino acid sequence of the K gene. FIG. 3 shows the base sequence of Ex promoter.

The mechanism of extracellular secretion may be that the K gene and Ex promoter make the outer membrane of *E. coli* more permeable, i.e., leaky, and polymeric substances present in a periplasmic space are accordingly discharged.

DNA regions equivalent to the K gene and Ex promoter, in terms of biological functions, may also be used. Equivalent regions may include, but are not limited to, regions with nucleotide replacement, nucleotide deletion, sequence inversion, and the like.

Plasmid pEAP7ΔP may be introduced into a proper host organism to transform it and may be replicated by proliferation of the transformant. Microorganisms commonly used in recombination technology may preferably be used as the host organism. Non-limiting example microorganisms are those bacteria belonging to the genus Escherichia, such as *E. coli* HB101, C600, DP, supF, 1776 and LE392. Representative of such *E. coli* is *E. coli* HB101 (D. S. Goldfarb et al. Proc. Natl. Acad. Sci. U.S.A., 79, 5886 (1982)), inheritance: pro, euB, B1, lacY, hsdR, hsdM, ara14, galkz, xyl5, mtl1, supE44, f−, endoI−, recA−, str).

The microorganism obtained by introducing plasmid pEAP7ΔP into E. coli HB101 is a novel microorganism, designated E. coli HB101 (pEAP7ΔP), which microorganism has been deposited with the Fermentation Research Institute, Agency of Industrial Science and Technology, Ministry of International Trade and Industry, Japan, International Depository Authority (hereinafter referred to as "FERM"), under accession number FERM BP-1101, on Jul. 29, 1985. The microbiological properties of E. coli HB101 (pEAP7ΔP) are the same as those of the DNA recipient host, E. coli HB101.

Plasmid pEAP7ΔP is used as a vector plasmid into which a DNA fragment coding for a useful, physiologically active substance is inserted. Thus, a plasmid capable of inducing extracellular secretion of a particular, useful, physiologically active substance in transformed host is obtained.

Representative examples of such plasmids are from a chromosomal DNA of Aeromonas sp. No. 212 has been inserted; (2) plasmid p7NK1 in which cellulase DNA (cel N) derived from a chromosomal DNA of Bacillus sp. No. N-4 has been inserted; and (3) plasmid p7FK1 in which cellulase DNA (cel F) derived from a chromosomal DNA of Bacillus sp. No. 1139 has been inserted.

Construction Of Plasmid p7AX2

Plasmid pAX1 containing a DNA fragment coding for xylanase and derived from a chromosomal DNA of Aeromonas sp. No. 212 (ATCC 31085) (Japanese Patent Application 278681/1984) is cleaved by restriction enzyme Bgl II, treated by E. coli DNA polymerase I (Klenow fragment) to change the cleavage face to a flush end and poured onto a 1% agarose gel. The gel is then subjected to electro-elution to isolate a DNA fragment of 4.0 kb containing xyl L DNA.

The isolated xyl L DNA fragment of 4.0 kb is added and ligated by DNA ligase T4 to Hinc II cleaved plasmid, pEAP7ΔP. The resultant plasmid is introduced into a host organism by a conventional technique to produce transformant organisms. A transformant organism having resistance to chloramphenicol and xylanase activity is screened and separated. Plasmid is prepared from the separated transformant to obtain plasmid p7AX2 containing xyl L DNA of about 4 kb.

Construction Of Plasmid p7NK1

Plasmid pNK1 containing a DNA fragment coding for cellulase and derived from chromosomal DNA of Bacillus sp. No. N-4 (ATCC 21833) (J. Bacteriol., 158, 503-506 (1984)) is digested by Hind III and treated in a similar way as in the case of plasmid p7AX2 to isolate a DNA fragment of 2.0 kb containing cel N DNA.

The isolated cel N DNA fragment of 2.0 kb is added and ligated by DNA ligase T4 to plasmid pEAP7ΔP digested by Hinc II. The resultant plasmid is introduced into a host organism by a conventional technique to produce transformant organisms. A transformant having resistance to chloramphenicol and cellulase activity is screened and separated. Plasmid is prepared from the separated transformant to obtain plasmid p7NK1 containing cel N DNA of about 2.0 kb.

Construction Of Plasmid p7FK1

Cel F DNA—Containing Plasmid pFK1

Chromosomal DNA of Bacillus sp. No. 1139 (Nippon Nogei Kagakukai, 1985 Annual Meeting (Sapporo), Summary, p.32 1B-28, p.707 2V-19) is cleaved by Hind III. The DNA fragments are inserted by a shotgun method into the Hind III site of vector plasmid pBR322, which is then introduced into E. coli HB101. A transformant having resistance to Ampicillin and cellulase activity is screened and separated. Plasmid pFK1 is obtained by a conventional method from the separated transformant. Plasmid pFK1 contains cel F DNA of 4.6 kb and is resistant to ampicillin.

The above plasmid pFK1, is digested by Hind III and Hinc II, and treated in a similar way as in the case of plasmid p7AX2 to isolate a DNA fragment of 2.9 kb containing cel F DNA.

The isolated cel F DNA fragment of 2.9 kb is then added and ligated by DNA ligase T4 to vector plasmid pEAP7ΔP cleaved by Hinc II. The resultant plasmid is introduced into a host organism by a conventional technique to produce a transformant. A transformant having resistance to chloramphenicol and cellulase activity is screened and separated. Plasmid is prepared from the separated transformant to obtain plasmid p7FK1 containing cel F DNA of about 2.9 kb.

The resultant plasmid, capable of inducing extracellular secretion of a useful, physiologically active substance in a transformed host, is introduced into a proper host organism by a conventional technique to obtain a transformant. The useful, physiologically active substance is obtained extracellularly in a remarkable amount by culturing the transformant. Microorganisms belonging to the genus Escherichia are used as host organisms. Microorganisms, such as E. coli HB101, C600, DP, supF, X 1776, and LE392, are preferably used. Typically used is E. coli HB101.

Microorganisms obtained by introducing plasmid p7AX2, p7NK1, or p7FK1, designated E. coli HB101 (p7AX2), E. coli HB101 (p7NK1), Escherichia coli HB101 (p7FK1), respectively, are novel and have been deposited with FERM on Jul. 29, 1985 under accession numbers FERM BP-1102, FERM BP-1103, and FERM BP-1104, respectively. The assignee, Rikagaku Kenkyusho, commits itself to maintain the deposited microorganisms for a period of thirty years from the filing date of the present application, that is, up to the year 2015, or for a period of five years from the date of the last request.

Microbiological properties of each microorganism thus obtained are the same as those of the HB101 strain of E. coli, which serve as the DNA recipient. The above procedure is shown in FIG. 4.

Production Of A Useful, Physiologically Active Substance

For culturing the transformants obtained in the above procedure, a culture medium appropriate for the production of substances, on a basis of particular genetic information, and able to support the growth of the host microorganism is used. Preferred culture media include an LB broth (tryptone, yeast extract NaCl), a BPB medium (Difco, polypeptone, yeast extract, potassium phosphate), a nutrient agar medium (Difco 0001), and a tryptone-sodium chloride medium, all of which are commonly used as growth media for E. coli.

In addition, nutrients such as amino acids and vitamins other than carbon sources and nitrogen sources may be added, if desired.

Culturing conditions of pH, temperature, amount of supplied oxygen, etc., are selected so as to support the growth of microorganisms of the genus Escherichia. After the microorganisms are inoculated to the medium, culturing is preferably continued in the same medium until the number of cells reaches a maximum, a late logarithmic growth phase, and production and accumulation of a high molecular substance in the medium substantially cease, a time range of from about 12 to about 48 hours. The pH is not particularly influential. However, a pH of from 5 to 8, particularly of 7, is appropriate.

According to the present invention, most of the physiologically active substance produced by the transformants is secreted into the culture medium outside the cells. The culture medium is filtered to form a filtrate and separated cells, and the filtrate is then treated according to conventional isolation and purification methods, such as ammonium sulfate fractionation, lyophilization, etc., to obtain the produced substance The separated cells are collected and extracted by centrifugation, sonication, etc., and again treated according to the same conventional isolation and purification methods to obtain an additional minor portion of the products.

Reference Example (Preparation Of Plasmid pEAP1)

(1) Preparation of chromosomal DNA coding for penicillinase production

Alkalophilic *Bacillus Sp.* No. 170 (FERM BP-467), which produces and secretes penicilinase, was cultured in a medium (glycerol 2.0 g/l, $K_2HPO_4$ 1.0 g/l, $MgSO_4.7H_2O$ 0.2 g/l, pH 9.0 by $NaHCO_3$ 10 g/l) at a temperature of 30° C. for 19 hours with shaking. Chromosomal DNA was extracted according to a phenol method and purified.

(2) Insertion of chromosomal DNA fragment into a vector

Ten μg of the chromosomal DNA obtained from step (1) was fragmented at 37° C. by the addition of restriction endonuclease EcoRI. Tetracycline resistant ($Tet^r$) plasmid pMB9 (Bethesda Research Laboratories, U.S.A.) was completely cleaved by EcoRI and heat treated at 65° C. for 5 minutes. The EcoRI cleaved plasmid pMB9 was then admixed with the fragmented chromosal DNA, subjected to a ligation reaction of DNA chains by a DNA ligase derived from T4 phage at 10° C. for 24 hours and heat treated at 65° C. for 5 minutes. Subsequently, two times the volume of ethanol was added to tee reaction solution to precipitate plasmid DNA in which the chromosomal DNA was inserted. The precipitated plasmid DNA was recovered.

(3) Transformation by plasmid pEAP1

The HB101 strain of *E. coli* (Molecular Cloning A Laboratory Manual P504 (1982)) (inheritance: $F^-$, hsdS20 ($r^-B$, $m^-B$), rec A13, ara$^-$14, pro A2, lac Y1, galK2, rps L20 ($Sm^1$), xyl-5, mtl-1, sup $E44\eta^-$), which is a hybrid strain of strain *E. coli* K-12 and strain *E. coli* B, was inoculated to 10 ml of LB broth (tryptone (Difco) 10 g/l, yeast extract 5 g/l, glucose 1 g/l, NaCl 10 g/l, pH 7.0), incubated at 37° C. with shaking until growth was in a late logarithmic growth phase and then collected. The collected cells were suspended in an ice-cold $CaCl_2$ solution at a final Ca concentration of 0.03M to prepare competent cells. The cell suspension was admixed with the plasmid DNA solution obtained in step (2) above, maintained under ice cooling for 60 minutes, and then heated to 42° C. for 1 to 2 minutes to allow the plasmid DNA to enter the cells and produce transformed strains.

The transformed strains were screened for drug resistance and a strain resistant to ampicillin (20 μg/ml) and tetracycline (50 μg/ml) was collected. A cell suspension of the collected drug-resistant strain was inoculated to LB broth and incubated at 37° C. for 3 to 5 hours with shaking. The inoculated cells were then collected and washed to yield a pEAP1 transformed strain of *E. coli* designated *E. coli* HB101 (pEAP1).

The *E. coli* HB101 (pEAP1) cells were treated as follows to obtain purified plasmid pEAP1:

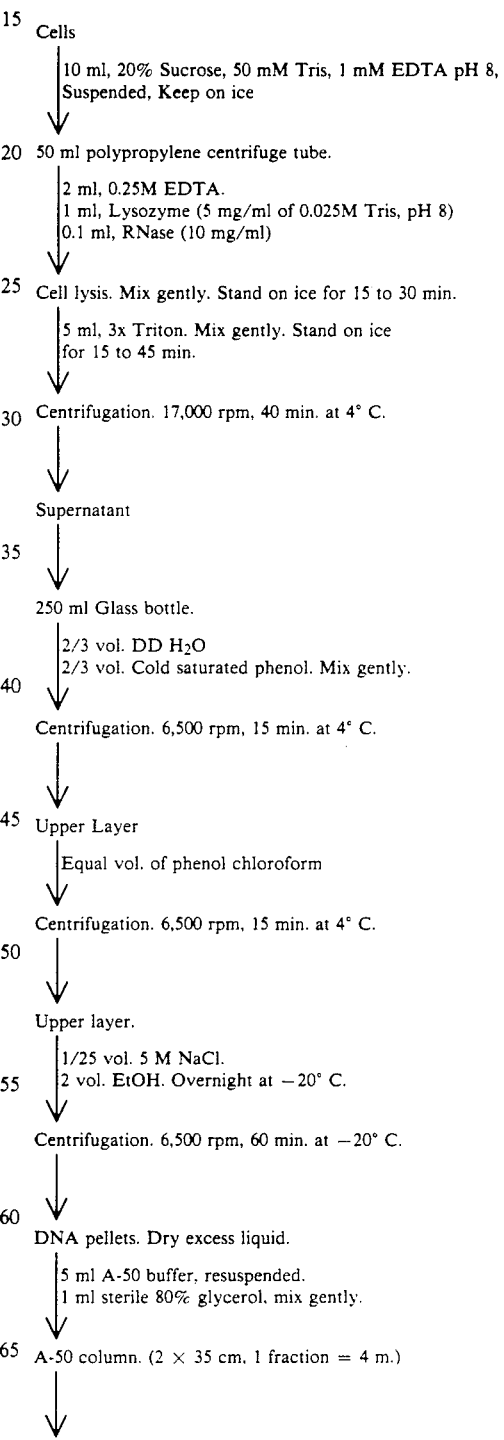

-continued

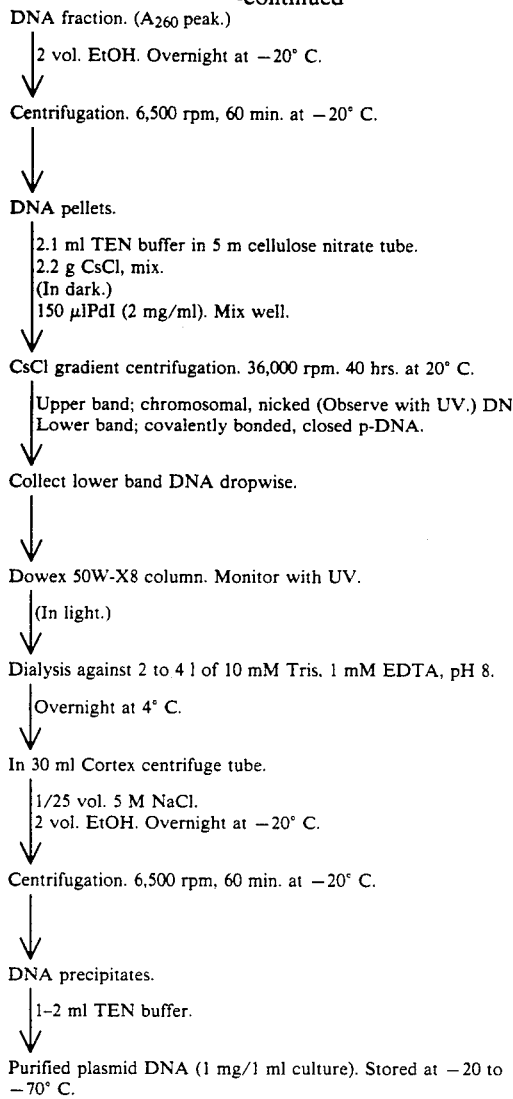

DNA fraction. (A₂₆₀ peak.)

2 vol. EtOH. Overnight at −20° C.

Centrifugation. 6,500 rpm, 60 min. at −20° C.

DNA pellets.

2.1 ml TEN buffer in 5 m cellulose nitrate tube.
2.2 g CsCl, mix.
(In dark.)
150 μlPdI (2 mg/ml). Mix well.

CsCl gradient centrifugation. 36,000 rpm. 40 hrs. at 20° C.

Upper band; chromosomal, nicked (Observe with UV.) DNA.
Lower band; covalently bonded, closed p-DNA.

Collect lower band DNA dropwise.

Dowex 50W-X8 column. Monitor with UV.

(In light.)

Dialysis against 2 to 4 l of 10 mM Tris. 1 mM EDTA, pH 8.

Overnight at 4° C.

In 30 ml Cortex centrifuge tube.

1/25 vol. 5 M NaCl.
2 vol. EtOH. Overnight at −20° C.

Centrifugation. 6,500 rpm, 60 min. at −20° C.

DNA precipitates.

1-2 ml TEN buffer.

Purified plasmid DNA (1 mg/1 ml culture). Stored at −20 to −70° C.

EXAMPLE 1 (Preparation of Plasmid pEAP3)

A mutant transformant, resistant to ampicillin (Ap$^r$), sensitive to tetracycline (Tc$^S$), and with enhanced penicillinase activity (about three times as strong as pEAP1), was obtained during passage of the strain *E. coli* HB101 (pEAP11). Plasmid was prepared from this Ap$^r$-Tc$^S$ mutant as in the Reference Example. Plasmid pEAP3 was obtained which lacked about 4 kb upstream of the structural gene of penicillinase.

EXAMPLE 2 (Preparation Of Plasmid pEAP6)

One μg of plasmid pEAP3, obtained as in Example 1, was cleaved by adding restriction enzymes EcoRI and Hind III and heating at 37° C. for 2 hours. *E. coli* DNA polymerase I (Klenow fragment) was then admixed to the cleaved plasmid and the admixture heated at room temperature for 30 minutes to change the DNA cleavage face to a flush end. The heated admixture was subjected to a ligation reaction using DNA ligase T4 at room temperature for 24 hours and then heat treated at 65° C. for 5 minutes. Two volumes of ethanol were added to precipitate and isolate plasmid DNA. The isolated plasmid DNA was introduced into *E. coli* HB101, as in the Reference Example, to produce transformants. Plasmid was isolated from am ampicillin resistant transformant and purified as in the Reference Example to yield plasmid pEAP6, which lacked an EcoRI-Hind III DNA fragment of about 1.0 kb.

EXAMPLE 3 (Preparation Of Plasmid pEAP7)

Ten μg of plasmid pBR329 (Gene, 17, 79 to 89 (1982)) were cleaved by adding restriction enzyme Acc II and heating at 37° C. for 24 hours. The heated, cleaved plasmid was layered onto a 1.5% agarose gel. A 1.3 kb Acc II DNA fraction was collected using an electro-elution method (P. J. Greene et al. "Methods In Molecular Biology" Vol. 7, Marcell Dekker), 1974 p.87). The collected DNA fragment contained a chloramphenicol acetyl transferase (CAT) gene.

One μg of plasmid pEAP6, obtained as in Example 2, was cleaved by adding restriction enzyme Sma I and heating at 37° C. for 2 hours. The heated, cleaved plasmid was admixed with 0.5 μg of the 1.3 kb Acc II DNA fragment and, after addition of DNA ligase T4, subjected to a ligation reaction at room temperature for 24 hours and then treated as in Example 2 to collect plasmid DNA. The collected plasmid DNA was introduced into *E. coli* HB101 to produce a transformant as in the Reference Example. A transformant resistant to chloramphenicol (50 μg/ml) and to ampicillin (20 μg/ml) was separated, and plasmid was isolated and purified as in Reference Example to obtain plasmid pEAP7.

EXAMPLE 4 (Preparation Of Plasmid pEAP7ΔP And Its Transformant)

On μg of plasmid pEAP7, obtained as in Example 3, was cleaved by adding restriction enzyme Hinc II and heating at 37° C. for 2 hours. The heated, cleaved plasmid was subjected to a ligation reaction of DNA chain at room temperature for 24 hours and then treated as in Example 2 to collect plasmid DNA. The plasmid DNA was introduced into *E. coli* HB101 to produce transformants as in the Reference Example. An ampicillin sensitive strain was separated from chloramphenicol resistant (50 μg/ml) transformants, and plasmid was isolated and purified as in the Reference Example to yield plasmid pEAP7ΔP.

Transformant *E. coli* HB101 (pEAP7ΔP) (FERM BP-1101) containing the plasmid pEAP7ΔP was inoculated to an LB broth and incubated at 37° C. for 3 to 5 hours to allow for proliferation.

EXAMPLE 5 (Preparation Of Plasmid p7AX2 And Its Transformant)

Ten μg of plasmid pAX1 were cleaved by adding restriction enzyme Bgl II and heating at 37° C. for 2 hours. *E. coli* DNA polymerase I (Klenow fragment) was admixed to the heated, cleaved plasmid and the admixture heated at room temperature for 2 hours to change the DNA cleavage face to a flush end. The heated admixture was poured onto a 1.5% agarose gel, and a xylanase DNA fraction of 4.0 kb collected by an electro-elution method.

One μg of plasmid pEAP7ΔP, obtained as in Example 4, was cleaved by adding restriction enzyme Hinc II and heating at 37° C. for 2 hours. The Bgl II DNA fragment of 4.0 kb (0.5 to 1 μg) was admixed to the heated, cleaved plasmid, the admixture subjected to ligation reaction by DNA ligase T4 at room temperature for 24 hours, treated as in Example 2, and plasmid DNA was collected. The collected plasmid DNA was introduced into E. coli HB101 to produce transformants, as in the Reference Example. Among transformants resistant to chloramphenicol (50 μg/ml), a strain having xylanase activity was separated. Plasmid was isolated and purified from the separated strain, as in the Reference Example, to yield plasmid p7AX2.

The transformant, E. coli HB101 (p7AX2) (FERM BP-1102, was inoculated to an LB broth and incubated at 37° C. for 3 to 5 hours with shaking to allow for proliferation.

EXAMPLE 6 (Preparation Of Plasmid p7NK1 And Its Transformant)

Ten μg of plasmid pNK1 were cleaved by adding restriction enzyme Hind III and heating at 37° C. for 24 hours. E. Coli DNA polymerase I (Klenow fragment) was admixed to the heated, cleaved plasmid and the admixture heated at room temperature for 24 hours to change the DNA cleavage face to a flush end. The heated admixture was poured onto a 1.5% agarose gel, and a cellulase DNA fragment of 2.0 kb was collected by an electro-elution method.

One μg of plasmid pEAP7ΔP, obtained as in Example 4, was cleaved by adding restriction enzyme Hinc II and heating at 37° C. for 2 hours. The cellulase DNA fragment of 2.0 kb (0.5 to 1 μg) was admixed to the heated, cleaved plasmid, and the admixture subjected to ligation reaction by DNA ligase T4 at room temperature for 24 hours, and then treated as in Example 2 to collect plasmid DNA. The collected plasmid DNA was introduced into E. coli HB101 to produce transformants as in the Reference Example. Among transformants resistant to chloramphenicol (50 μg/ml), a strain having cellulase activity was separated. Plasmid was isolated and purified from the separated strain as in the Reference Example to obtain plasmid p7NK1.

The transformant, E. coli HB101 (p7NK1) (FERM BP-1103) was inoculated to an LB broth and incubated at 37° C. for 3 to 5 hours with shaking to allow for proliferation.

EXAMPLE 7 (Preparation Of Plasmid p7FK1 And Its Transformant)

Ten μg of plasmid pFK1 were cleaved by adding restriction enzymes Hind III and Hinc II and heating at 37° C. for 2 hours. E. coli polymerase I (Klenow fragment) was admixed to the heated, cleaved plasmid and the admixture heated at room temperature for 2 hours to change the DNA cleavage face to a flush end. The heated admixture was poured onto a 1.5% agarose gel, and a cellulase DNA fragment of 2.9 kb was collected by an electro-elution method.

One μg of plasmid pEAP7μP, obtained as in Example 4, was cleaved by adding restriction enzyme Hinc II and heating at 37° C. for 2 hours. The cellulase DNA fragment of 2.9 kb was admixed to the heated, cleaved plasmid, subjected to ligation reaction by DNA ligase T4 at room temperature for 24 hours, and then treated as in Example 2 to collect plasmid DNA. The collected plasmid DNA was introduced into E. coli HB101 to produce transformants. Among transformants resistant to chloramphenicol (50 μg/ml), a strain having cellulase activity was separated. Plasmid was isolated and purified from the separated strain as in the Reference Example to obtain plasmid p7FK1.

The transformant, E. coli HB101 (p7FK1) (FERM BP-1104), was inoculated to an LB broth and incubated at 37° C. for 3 to 5 hours with shaking to allow for proliferation.

EXAMPLE 8 (Production And Extracellular Secretion By Each Transformant)

Microorganism

Transformants obtained as in Examples 5 to 7:

| | |
|---|---|
| E. coli | HB101 (p7AX2) (FERM BP-1102) |
| E. coli | HB101 (p7NK1) (FERM BP-1103) |
| E. coli | HB101 (p7FK1) (FERM BP-1104) | were used and examined for distribution of intracellular, periplasmic space, and extracellular production of xylanase and cellulase. For comparison, E. coli HB101 strains which were transformed by the below-listed plasmids pAX2, pNK1, or pFK1 were used

| | |
|---|---|
| pAX2: | a Bgl II DNA fragment of 4.0 Kb containing xyl L, $Ap^r$, $Xyl^+$ was integrated in a Bam HI restriction site of pBR322. |
| pNK1: | pBR322+ Hind III DNA fragment of 2.0 Kb containing cel N, $AP^r$, $Cel^+$. |
| pFK1: | pBR322+ Hind III DNA fragment of 4.6 Kb containing cel F, $AP^r$, $Cel^+$. |

Medium

An LB broth having the following composition was used for culturing:

10 g of tryptone; 5 g of yeast extract; 1 g of glucose, 10 g of NaCl; 1l of distilled water. pH was regulated by the addition of NaOH. If necessary, 20 g of agar was added to prepare a solid medium.

Culturing Method

Each of the transformants was inoculated to the above LB broth and cultured at 37° C. for 24 hours in a 500 ml capacity flask. After collecting cells, the products were fractionated into an extracellular, a periplasmic space, and an intracellular fraction using an osmotic shock method (Kato et al., Eur. J. Appl. Microbiol. Biotechnol (1983) 18:339-343).

Determination Of Enzyme Activity

Xylanase activity: A xylan solution (0.1 ml) (Seikagaku Kogyho Co.) and 0.1 ml of a 0.2 M tris maleate buffer of pH 8.0 were admixed with 0.05 ml of an enzyme solution and the admixture heated at 40° C. for 10 minutes. One ml of DNS (3.5-dinitrosalicylic acid) was then added to the xylan-enzyme solution and the admixture heated at 100° C. for 5 minutes. Then, 4 ml of water were added to the heated mixture and absorbance determined at 510 nm. An amount of enzyme that reduced 1 mg of xylose in one minute was designated 1 unit (U) of xylanase.

Cellulase activity: One ml of carboxymethyl cellulose (CMC) (2.0%) and 1 ml of glycine NaCl-NaOH buffer (pH 9.0) were admixed with 0.5 ml of an enzyme solution and the admixture heated at 40° C. for 20 minutes. Reducing sugars were quantified by a (DNS) method. That is, one ml of a 3.5-dinitro-salicylic acid (DNS) agent was added to 0.25 ml of the heated glycine-CMC-enzyme admixture and the mixture heated at 100° C. for 5 minutes to allow for color development. After cooling, the DNS-CMC mixture was diluted with 4 ml of distilled water. The diluted mixture was subjected to colorimetric quantitative analysis at a wavelength of 500 nm.

One unit (U) of enzyme activity is defined as the amount of enzyme that reduces 1 μmol of dextrose in 1 minute in the above conditions.

The results are shown in Table 1.

TABLE I

| Plasmid | Enzyme Protein | Extracellular Enzyme Activity (U/ml) | Periplasmic Enzyme Activity (U/ml) | Intracellular Enzyme Activity (U/ml) | Total Enzyme Activity (U/ml) |
|---|---|---|---|---|---|
| pAX2 | Xylanase | 23 (4.8%) | 147 (30.4%) | 315 (64.8%) | 485 |
| p7AX2 | | 135 (62.1%) | 8 (3.6%) | 74 (34.3%) | 217 |
| pNK1 | Cellulase | 12 (9.2%) | 60 (44.0%) | 64 (46.8%) | 136 |
| p7nk1 | | 282 (66.7%) | 92 (21.8%) | 49 (11.5%) | 423 |
| pFK1 | Cellulase | 7 (6.1%) | 88 (74.3%) | 23 (19.6%) | 118 |
| p7FK1 | | 93 (60.2%) | 16 (10.6%) | 45 (29.2%) | 154 |

EFFECTS OF THE INVENTION

According to the resent invention, a plasmid containing a DNA region capable of inducing extracellular secretion of a useful, physiologically active substance in a transformed host and a promoter DNA region which regulates expression of the former DNA region is used. By inserting a DNA fragment coding for the useful, physiologically active substance into the above plasmid, a plasmid is obtained which has the ability of providing a host, originally having no ability of extracellular secretion, with the capability of inducing the production and secretion of the useful, physiologically active substances in the transformed host. Accordingly, it is possible by the present invention to optionally prepare a plasmid which is capable of producing and extracellularly secreting useful, physiologically active substances, such as insulin, human growth hormone, interferons, and enzymes. By introducing this plasmid into a host such as E. coli, it is possible to create useful microorganisms which have a function of promoting extracellular secretion of the above useful, physiologically active substances.

We claim:

1. A plasmid comprising a DNA sequence encoding the kil gene as set forth in FIG. 2 directly and operably linked to the Ex promoter derived from Bacillus sp. No. 170.

2. The plasmid according to claim 1, wherein said Ex promoter has a nucleotide sequence as shown in FIG. 3.

3. A process for producing a heterologous protein, which comprises:
(a) transforming a microorganism with a plasmid wherein said plasmid comprises (i) the kil gene of FIG. 2 directly and operatively linked to the Ex promoter derived from Bacillus sp. No. 170, (ii) a genetic marker, and (iii) a DNA fragment encoding a heterologous protein;
(b) culturing said microorganism under suitable conditions for the production and secretion of the heterologous protein to the culture medium; and
(c) isolating the heterologous protein from the culture medium.

4. The process according to claim 3, wherein the heterologous protein is xylanase.

5. The process according to claim 3, wherein the heterologous protein is cellulase.

6. The process according to claim 3, wherein the transformed microorganism is *Escherichia coli* HB101 (p7AX2).

7. The process according to claim 3, wherein the transformed microorganism is *Escherichia coli* HB101 (p7NK1).

8. The process according to claim 3, wherein the transformed microorganism is *Escherichia coli* HB101 (p7FK1).

9. The process according to claim 3, wherein said plasmid containing the DNA fragment coding for the heterologous protein is a plasmid selected from the group consisting of p7AX2, p7FK1 and p7NK1.

10. *Escherichia coli* HB101 (pEAP7ΔP).

11. *Escherichia coli* HB101 (p7AX2).

12. *Escherichia coli* HB101 (p7NK1).

13. *Escherichia coli* HB101 (p7FK1).

* * * * *

UNITED STATES PATENT AND TRADEMARK OFFICE
CERTIFICATE OF CORRECTION

PATENT NO. : 5,246,839
DATED : September 21, 1993
INVENTOR(S) : Koki Horikoshi et al.

It is certified that error appears in the above-identified patent and that said Letters Patent is hereby corrected as shown below:

Col. 3, lines 12, 19 & 43 "*Bacillus sq.*" should be -- *Bacillus sp.* --.

Col. 4, line 3, "Ap" should be -- $Ap^r$ --.

Col. 5, line 18, after "are" insert -- (1) plasmid p7AX2 in which xylanase DNA (xyl L) derived --.

Col. 7, line 49, "tee" should be -- the --.

Col. 9, line 50, "(pEAP11)" should be -- (pEAP1) --.

Signed and Sealed this

Twenty-sixth Day of July, 1994

BRUCE LEHMAN

Attest:

*Attesting Officer*    *Commissioner of Patents and Trademarks*